US010045743B2

(12) United States Patent
Grant et al.

(10) Patent No.: US 10,045,743 B2
(45) Date of Patent: Aug. 14, 2018

(54) METHOD FOR GENERATING A VIRTUAL X-RAY PROJECTION ON THE BASIS OF AN IMAGE DATA SET OBTAINED WITH AN X-RAY IMAGING DEVICE, COMPUTER PROGRAM, DATA CARRIER AND X-RAY IMAGING DEVICE

(71) Applicant: Siemens Aktiengesellschaft, Munich (DE)

(72) Inventors: Katharine Lynn Rowley Grant, Rochester, MN (US); Rainer Raupach, Heroldsbach (DE); Bernhard Schmidt, Fuerth (DE); Martin Sedlmair, Zirndorf (DE)

(73) Assignee: SIEMENS AKTIENGESELLSCHAFT, Munich (DE)

( * ) Notice: Subject to any disclaimer, the term of this patent is extended or adjusted under 35 U.S.C. 154(b) by 114 days.

(21) Appl. No.: 15/131,251

(22) Filed: Apr. 18, 2016

(65) Prior Publication Data

US 2016/0302751 A1 Oct. 20, 2016

(30) Foreign Application Priority Data

Apr. 20, 2015 (DE) .................. 10 2015 207 107

(51) Int. Cl.
*G06T 11/00* (2006.01)
*A61B 6/00* (2006.01)
*A61B 6/03* (2006.01)

(52) U.S. Cl.
CPC .............. *A61B 6/032* (2013.01); *A61B 6/482* (2013.01); *A61B 6/50* (2013.01); *A61B 6/5205* (2013.01);

(Continued)

(58) Field of Classification Search
CPC .......... A61B 6/032; A61B 6/482; A61B 6/50; A61B 6/5205; A61B 6/461; A61B 6/467; G06T 11/00; G06T 2207/10124
See application file for complete search history.

(56) References Cited

U.S. PATENT DOCUMENTS

| 6,549,645 B1 * | 4/2003 | Oikawa ................. G06T 11/008 382/132 |
| 2002/0136440 A1 * | 9/2002 | Yim ........................ G06T 17/20 382/131 |

(Continued)

FOREIGN PATENT DOCUMENTS

DE 102010040096 A1 3/2012

OTHER PUBLICATIONS

Williamson, Jeffrey F. et al.: "On two-parameter models of photon cross sections: Application to dual-energy CT imaging", in: Med. Phys., vol. 33, No. 11, Nov. 2006, pp. 4115-4129, DOI: 10.1118/1.2349688.

(Continued)

*Primary Examiner* — Jon Chang
(74) *Attorney, Agent, or Firm* — Harness, Dickey & Pierce, P.L.C.

(57) ABSTRACT

An embodiment relates to a method for generating a virtual X-ray projection of at least one body region of a patient to be imaged with an X-ray imaging device, a machine-readable data carrier and/or an X-ray imaging device. The method includes acquiring at least one projection data set representing the at least one body region of the patient to be imaged; reconstructing an image data set from the at least one projection data set, the image data set representing local X-ray attenuation values in the at least one body region; replacing at least one local X-ray attenuation value by a modified X-ray attenuation value; forward projecting the modified image data set onto a virtual X-ray radiation (Continued)

detector; calculating intensity values for a plurality of detector elements from the modified projection data set; transforming the calculated intensity values into scan values; and assigning the scan values to an image matrix.

31 Claims, 3 Drawing Sheets

(52) U.S. Cl.
CPC .............. *A61B 6/542* (2013.01); *G06T 11/00* (2013.01); *A61B 6/461* (2013.01); *A61B 6/467* (2013.01); *G06T 2207/10124* (2013.01)

(56) References Cited

U.S. PATENT DOCUMENTS

| | | | |
|---|---|---|---|
| 2007/0291895 A1* | 12/2007 | Yin | A61B 6/025 378/20 |
| 2009/0121142 A1* | 5/2009 | Heismann | G01T 1/2018 250/363.04 |
| 2011/0293161 A1* | 12/2011 | Yi | G06T 11/005 382/131 |
| 2013/0162645 A1 | 6/2013 | Ulrici | |

OTHER PUBLICATIONS

Lee Young Han et al.: "Metal artifact reduction in gemstone spectral imaging dual-energy CT with and without metal artifact reduction software", European Radiology vol. 22 No. 6; pp: 1331-1340; 2012.

\* cited by examiner

METHOD FOR GENERATING A VIRTUAL X-RAY PROJECTION ON THE BASIS OF AN IMAGE DATA SET OBTAINED WITH AN X-RAY IMAGING DEVICE, COMPUTER PROGRAM, DATA CARRIER AND X-RAY IMAGING DEVICE

PRIORITY STATEMENT

The present application hereby claims priority under 35 U.S.C. § 119 to German patent application number DE 102015207107.3 filed Apr. 20, 2015, the entire contents of which are hereby incorporated herein by reference.

FIELD

At least one embodiment of the invention generally relates to a method for generating one or more X-ray projections on the basis of an image data set obtained via an X-ray image recording device and representing local X-ray attenuation values of at least one body region to be imaged of a patient, wherein at least one local X-ray attenuation value is replaced by a modified X-ray attenuation value. At least one embodiment of the invention further generally relates to a corresponding computer program, corresponding data carriers and/or a corresponding X-ray imaging device for realizing at least one embodiment of the method according to the invention.

BACKGROUND

For the clarification of medical questions or for interventional radiology, X-ray imaging devices, for example a C-arm X-ray device or a computed tomography device, are being used ever more frequently. It is common to X-ray imaging devices that they have an X-ray radiation source, typically an X-ray tube, and an X-ray radiation detector cooperating with the X-ray radiation source. The X-ray radiation emitted by the X-ray radiation source passes through a patient to be investigated and is attenuated by interaction with the different tissue types of the patient. The detector is arranged behind the patient in relation to the X-ray radiation source, absorbs the X-ray radiation remaining behind the patient and converts it into the electrical signal corresponding to the X-ray attenuation caused by the patient.

The X-ray radiation source emits X-ray radiation with an emission spectrum, that is, the gamma quanta emitted by the X-ray radiation source typically have an energy distribution comprising a plurality of quantum energy values. The X-ray radiation emitted is therefore polychromatic. The emission spectrum is substantially influenced by the X-ray tube voltage or the acceleration voltage with which the X-ray radiation source is operated. Generalizing, it can be stated that the higher the acceleration voltage is, the greater also is the mean X-ray quantum energy of the emission spectrum.

It is known that different materials or tissue types, for example, water or bone interact to different extents with X-ray radiation. Simply expressed, the image contrast of all X-ray images is based on these differences. Furthermore, the energy-dependency of the X-ray attenuation when passing through material is also known. Lower energy X-ray radiation is more strongly absorbed by matter than higher energy X-ray radiation. These differences in the interaction of X-ray radiation with matter must be taken into account in X-ray imaging in order to generate X-ray image recordings which have sufficient image quality to answer the medical questions and also to protect the patient against unnecessary dosage exposure.

Depending on the case, superimposition images or sectional images of an object or a patient can be generated with an X-ray imaging device. In order to generate classic X-ray superimposition images, the object to be imaged is irradiated by an X-ray radiation source in one direction and imaged on an X-ray film or via an X-ray radiation detector. A projection of the imaged volume is created on a surface. Image parts of the irradiated volume lying one after another in the radiation direction become superimposed. Whether the X-ray attenuation visible in the superimposition image was caused by a material of relatively great X-ray absorption or by a greater layer thickness cannot be distinguished from the image.

A topogram, for example, which is also known as a scout view corresponds to such a classical, two-dimensional X-ray superimposition recording. It measures the individual X-ray attenuation distribution of a patient in the particular projection direction, typically in a lateral or anterior-posterior direction and forms this on the basis of different gray values.

For the generation of a sectional image, X-ray attenuation profiles of an object are measured from many different projection directions and therefrom, the three-dimensional volume structure of the object is reconstructed. By way of a computer-assisted image reconstruction which can be carried out, for example, with the algorithm of the filtered, weighted back projection, for each volume element of the object, a so-called voxel, the X-ray attenuation level is determined and therefrom, the sectional image is calculated. The sectional image corresponds to a transverse section through the examination object, wherein the section typically lies in a plane parallel to or substantially parallel to the X-rays used for generating the projection data. With a plurality of successive circulations of the X-ray radiation source round the object, mutually adjacent sectional images can be generated. A plurality, for example, several hundred individual images together form a volume rendering of the object.

An advantage of computed tomography, abbreviated to CT as compared with conventional projection X-ray imaging, is that superimposition-free representations can be generated. Imaging precision and detail accuracy are correspondingly higher in CT sectional images. In some cases however, apart from a CT data set, an additional X-ray projection is desirable. With the aid of a topogram, for example, the X-ray dose for a CT scan can be adapted particularly well to a patient. On the other hand, a trained person can draw from the X-ray projection particular information concerning the imaged object "at a glance" which could only be drawn from a CT data set typically containing a large quantity of data at the cost of much effort and time.

SUMMARY

The inventors have recognized that it is disadvantageous that the X-ray projection recording causes, alongside the actual CT scan an additional non-trivial proportion of the total dose for the patient.

The inventors have recognized that in order to circumvent this problem, X-ray projections can be generated from existing CT data sets. Although these artificially generated projections show a geometrically correct projection of the body region to be imaged, the gray values represented are typically not comparable with those of real X-ray projections generated by way of X-ray film or X-ray detectors. This applies even if, in place of line integrals, exponential intensity-representing values of the line integrals are imaged. Causes for this lie predominantly in the emission spectrum of the X-ray radiation source deviating from a real projection recording of the X-ray radiation source in the CT data recording or other deviating recording parameters. In addition thereto is the fact that the CT data set is artifact-laden due to the previously run sectional image reconstruction or is falsified through corrections such as scattered ray correction, ray hardening correction or truncation correction such that the X-ray projections subsequently generated therefrom are also error-laden.

In contrast to this, at least one embodiment of the present invention is directed to an improvement of X-ray projections generated from an existing CT data set. These improved X-ray projections are distinguished firstly by their gray-value distribution which comes very close to an actually recorded X-ray projection or, secondly, by their increased information content in relation to a body region of the patient being imaged.

At least one embodiment of the invention is directed to a method, a computer program, a machine-readable data carrier and/or an X-ray imaging device.

At least one embodiment of the invention is described below in relation to the claimed method and also in relation to the claimed device. Features, advantages or alternative embodiments mentioned herein are also applicable similarly to the other claimed subject matter and vice versa. In other words, the present claims (which are directed, for example, to a device) can also be further developed with features disclosed or claimed with regard to a method. The corresponding functional features of the method are herein configured by suitable modules or units.

At least one embodiment of the invention is based on the acquisition of at least one projection data set representing at least one body region of a patient with the X-ray imaging device and the reconstruction of an image data set from the at least one projection data set, wherein the image data set represents local X-ray attenuation values in the at least one body region of the patient to be imaged. The inventors have recognized that this image data set can be modified in that at least one local X-ray attenuation value is replaced by a modified X-ray attenuation value. From this modified image data set, a modified projection data set is subsequently generated in that the modified image data set is forward projected while taking account of a virtual projection geometry onto a virtual X-ray radiation detector. From the modified projection data set, subsequently, taking account of the virtual projection geometry, intensity values are calculated for a plurality of detector elements of the virtual X-ray radiation detector which, in a further step, are transformed into scan values output by the virtual X-ray radiation detector, which are then assigned to an image matrix for imaging or generating a virtual X-ray projection.

At least one embodiment of the invention is based on the acquisition of at least one projection data set representing at least one body region of a patient with the X-ray imaging device and the reconstruction of an image data set from the at least one projection data set, wherein the image data set represents local X-ray attenuation values in the at least one body region of the patient to be imaged. The inventors have recognized that this image data set can be modified in that at least one local X-ray attenuation value is replaced by a modified X-ray attenuation value. From this modified image data set, a modified projection data set is subsequently generated in that the modified image data set is forward projected while taking account of a virtual projection geometry onto a virtual X-ray radiation detector. From the modified projection data set, subsequently, taking account of the virtual projection geometry, intensity values are calculated for a plurality of detector elements of the virtual X-ray radiation detector which, in a further step, are transformed into scan values output by the virtual X-ray radiation detector, which are then assigned to an image matrix for imaging or generating a virtual X-ray projection.

At least one embodiment of the invention also relates to a computer program with program code for carrying out all the method steps in accordance with the method according to at least one embodiment of the invention when the program is run in a computer. As a result, the method can be carried out reproducibly and in a less error-prone way on different computers.

At least one embodiment of the invention relates also to a machine-readable data carrier on which the computer program described above is stored.

At least one embodiment of the invention also relates to an X-ray imaging device for generating a virtual X-ray projection of at least one body region of a patient to be imaged, wherein the X-ray imaging device comprises an X-ray module comprising at least one X-ray radiation source for generating and emitting X-ray radiation in each case with a pre-determined X-ray quantum energy distribution, a detector module comprising at least one X-ray radiation detector for detecting X-ray radiation emitted by the X-ray radiation module and a computer system which, during operation, carries out the method steps as per the method according to at least one embodiment of the invention. The X-ray imaging device is an X-ray device which is configured to record a plurality of X-ray projections from different projection angles, for example, a computed tomography device with a ring-shaped rotating frame or a C-arm X-ray device. The recordings can be generated during a, particularly continuous, rotation movement of a recording unit comprising the X-ray module and a detector module cooperating with the X-ray radiation source. An X-ray radiation source can be, in particular, an X-ray tube with a rotating anode. An X-ray radiation detector for a computed tomography device is, for example, a linear detector with a plurality of rows. An X-ray radiation detector for a C-arm X-ray device is, for example, a flat detector. The X-ray detector can be configured so as to be both energy-resolving and counting.

At least one embodiment of the invention also relates to an X-ray imaging device for generating a virtual X-ray projection of at least a body region of a patient to be imaged, wherein the X-ray imaging device comprises the following units: an X-ray module comprising at least one X-ray radiation source for generating and emitting X-ray radiation, in each case, having a pre-determinable X-ray quantum energy distribution, a detector module comprising at least one X-ray radiation detector for detecting X-ray radiation emitted by the X-ray radiation module, and a computer system comprising an interface unit which is configured to acquire at least one projection data set representing the at least one body region of the patient to be imaged, a reconstruction unit which is configured to reconstruct an image data set from the at least one projection data set, wherein the image data set represents local X-ray attenuation values in the at least one body region of the patient to be imaged, a modification unit which is configured to modify the image data set such that at least one local X-ray attenuation value is replaced by a modified X-ray attenuation value, a projection unit which is configured to generate a modified projection data set by forward projection of the modified image data set to a virtual X-ray radiation detector, taking account of a virtual projection geometry, a calculation unit which is configured to calculate intensity values for a plurality of detector elements of the virtual X-ray radiation detector from the modified projection data set, taking account of the virtual projection geometry, a transformation unit which transforms the calculated intensity values into scan values output by the virtual X-ray radiation detector and an assigning unit which assigns the scan values to an image matrix.

BRIEF DESCRIPTION OF THE DRAWINGS

The invention will now be described and explained in greater detail making reference to the example embodiments illustrated in the drawings, in which.

DETAILED DESCRIPTION OF THE EXAMPLE EMBODIMENTS

Figure 1:
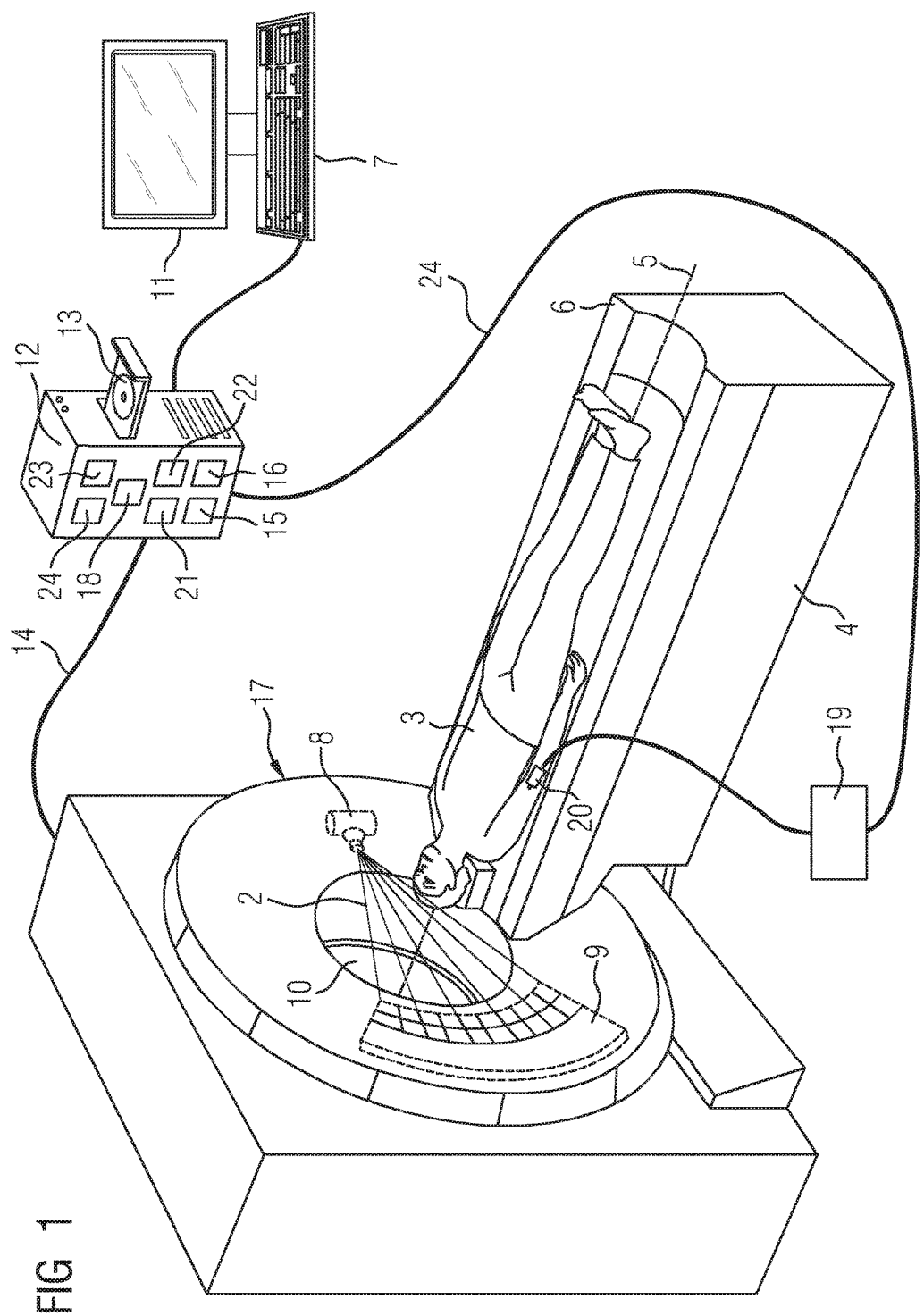
FIG. 1 shows an X-ray imaging device according to an example embodiment of the invention.

The drawings are to be regarded as being schematic representations and elements illustrated in the drawings are not necessarily shown to scale. Rather, the various elements are represented such that their function and general purpose become apparent to a person skilled in the art. Any connection or coupling between functional blocks, devices, components, or other physical or functional units shown in the drawings or described herein may also be implemented by an indirect connection or coupling. A coupling between components may also be established over a wireless connection. Functional blocks may be implemented in hardware, firmware, software, or a combination thereof.

Various example embodiments will now be described more fully with reference to the accompanying drawings in which only some example embodiments are shown. Specific structural and functional details disclosed herein are merely representative for purposes of describing example embodiments. The present invention, however, may be embodied in many alternate forms and should not be construed as limited to only the example embodiments set forth herein.

Accordingly, while example embodiments of the invention are capable of various modifications and alternative forms, embodiments thereof are shown by way of example in the drawings and will herein be described in detail. It should be understood, however, that there is no intent to limit example embodiments of the present invention to the particular forms disclosed. On the contrary, example embodiments are to cover all modifications, equivalents, and alternatives falling within the scope of the invention. Like numbers refer to like elements throughout the description of the figures.

Before discussing example embodiments in more detail, it is noted that some example embodiments are described as processes or methods depicted as flowcharts. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing example embodiments of the present invention. This invention may, however, be embodied in many alternate forms and should not be construed as limited to only the embodiments set forth herein.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items. The phrase "at least one of" has the same meaning as "and/or".

Further, although the terms first, second, etc. may be used herein to describe various elements, components, regions, layers and/or sections, it should be understood that these elements, components, regions, layers and/or sections should not be limited by these terms. These terms are used only to distinguish one element, component, region, layer, or section from another region, layer, or section. Thus, a first element, component, region, layer, or section discussed below could be termed a second element, component, region, layer, or section without departing from the teachings of the present invention.

Spatial and functional relationships between elements (for example, between modules) are described using various terms, including "connected," "engaged," "interfaced," and "coupled." Unless explicitly described as being "direct," when a relationship between first and second elements is described in the above disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Spatially relative terms, such as "beneath", "below", "lower", "above", "upper", and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, term such as "below" can encompass both an orientation of above and below. The device may be otherwise oriented (rotated 90 degrees or at other orientations) and the spatially relative descriptors used herein are interpreted accordingly.

Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/hardware, that manipulates and transforms data represented as physical, electronic quantities within the computer system's registers and memories into other data similarly represented as physical quantities within the computer system memories or registers or other such information storage, transmission or display devices.

A virtual X-ray projection should be understood as a two-dimensional X-ray projection or X-ray superimposition recording in the classic sense of X-ray imaging. This is virtual because it is not recorded or generated directly via an X-ray imaging device, but is calculated from a previously existing image data set. The virtual X-ray projection can be calculated or generated in any desired projection direction. In one example of the present invention, the virtual X-ray projection is generated in the anterior-posterior or the lateral direction and thus corresponds in its direction to a classic topogram.

The at least one projection data set describes at least one set of raw data which is acquired via an X-ray imaging device for representing the at least one body region of the patient to be imaged. The projection data set thus comprises a plurality of X-ray attenuation profiles of the at least one body region of the patient recorded from different projection directions. The projection data set comprises at least the number of X-ray attenuation profiles necessary for the reconstruction of a sectional image. A projection data set is, in particular, a computed tomography data set. It can be acquired via a computed tomography device or a C-arm device. In the case of at least two projection data sets, they can differ, for example, in respect of the X-ray quantum energy distribution of the respective X-ray radiation taken into account, as described in greater detail below.

The at least one projection data set can relate to a subregion of the body of the patient, specifically the at least one body region of the patient which is to be imaged via an X-ray imaging device. In this case, the projection data set contains information relating to the X-ray attenuation distribution of the patient only regarding the subregion to be imaged, for example, regarding the thorax or the pelvis. The projection data set relates alternatively to the whole body of the patient. In this case, the projection data set contains information relating to the X-ray attenuation distribution of the patient in relation to the whole body.

An image data set describes the three-dimensional image data representing local X-ray attenuation values at least in the body region of the patient to be imaged, which is produced by known reconstruction algorithms such as a weighted, filtered back-projection or an iterative reconstruction method from the at least one projection data set. The image data set and the at least one projection data set can be substantially transformed into one another through the use of a reconstruction algorithm or the reverse calculation operations, for example, forward and back-projection steps. Herein, the reconstruction involves, in particular, a "neutral reconstruction", which means that the reconstruction algorithm comprises no contrast-enhancing operations such as edge-enhancing or artifact correction measures. In the case of at least two projection data sets, the image data set can be reconstructed on the basis of both projection data sets. Herein, for example, information from both projection data sets can be taken into account with weighting factors according to a medical problem. The projection data set comprises at least the image data necessary for representing a sectional image.

The image data set represents an X-ray attenuation caused by interaction of the X-ray radiation with the patient tissue in at least the body region of the patient to be imaged. Due to the material composition of the patient body in the body region to be imaged, the X-ray attenuation has a distribution which is described by local X-ray attenuation values. A local X-ray attenuation value is to be understood herein as the X-ray attenuation value associated in the image data set with a volume element of the patient body. The minimum size or the minimum extent of a volume element is determined by the spatial resolution of the detectors used for the X-ray scan and by the scan geometry. A volume element corresponds in the simplest case to a voxel of the image data set. The local X-ray attenuation value can also take account of the X-ray attenuation values of a plurality of adjacent image elements in the image data set and can be obtained, for example, as a mean value therefrom. A volume element is then correspondingly larger.

A modified X-ray attenuation value is also an X-ray attenuation value associated with a volume element of the patient body, although as distinct from a local X-ray attenuation value, this is not measured but is obtained by other devices as described in detail below. At least one local X-ray attenuation value is exchanged in the image data set with a modified X-ray attenuation value, such that a modified image data set is produced.

The X-ray projection is generated from the modified image data set in that this is forward-projected onto a virtual X-ray radiation detector according to a virtual projection geometry. This calculation step simulates the generation of a real X-ray projection by irradiation of the patient with real X-ray radiation. Herein, a superimposition of the local X-ray attenuation values takes place. Line integrals are calculated over the local X-ray attenuation values along selected X-ray radiation paths. The integration lines correspond to virtual X-ray paths which each start in a focus point, that is, a virtual X-ray radiation source and end in a detector element of a virtual X-ray radiation detector. The virtual X-ray radiation detector herein corresponds in its imaging properties, its geometry and its position or arrangement to the X-ray radiation detector which would be put to use for an actual recording of an X-ray projection. It can be assumed, for example, to be a detector with a planar or curved detection surface, as a linear detector or as a detector with a plurality of columns and rows. The virtual projection geometry should be understood as the imaging geometry assumed for the forward projection which takes account of the focus point of the virtual X-ray radiation, the position and extent of the virtual X-ray radiation detector and the ray paths of the virtual X-ray radiation resulting therefrom, and/or the resulting integration lines.

The assumption which applies for the type and embodiment of the virtual X-ray radiation detector (planar/curved, single-line or multi-line detector, etc.), the virtual X-ray radiation source (isotropic/anisotropic source, shaping filter, etc.) and the projection geometry also determines the intensity of the X-ray radiation falling on a single detector element of the virtual X-ray radiation detector. For a plurality, that is, at least two detector elements, in one step of the method according to an embodiment of the invention, taking account of the virtual projection geometry and the corresponding overlaid X-ray attenuation, an intensity value is determined. This calculation is carried out under the assumption of an X-ray radiation intensity originating from the X-ray radiation source with which the at least one body region of the patient would have been irradiated during an actual X-ray projection recording. This starting intensity is pre-determinable.

Taking account of an imaging characteristic that is specific to the simulated virtual X-ray radiation detector, scan values are calculated from the intensity values for the plurality of detector elements, as they would be output by a real radiation detector corresponding to the virtual X-ray radiation detector. These scan values are finally assigned to an image matrix which, in the simplest case, corresponds in the number of rows and columns to the virtual detector.

At least one embodiment of the invention is based on the concept that the quality of a virtual X-ray projection can be increased by the substitution of at least one suitably selected modified X-ray attenuation value. The stipulation of the modified X-ray attenuation value can take place in a variety of ways. Thus, it can be advantageous to determine the modified X-ray attenuation value such that the virtual X-ray projection provides a particularly realistic image impression for the observer, as would be obtained with an actual X-ray projection recording. In another situation, through the modification of at least one local X-ray attenuation value, an emphasis or falsification of particular image information that is desired or can be of great usefulness takes place. In both cases, the method steps also bring about a modeling or simulation of the signal chain of an actual X-ray projection recording with an X-ray imaging device that is accurate in detail.

According to a first embodiment of the invention, the modification of the image data set comprises assigning the at least one local X-ray attenuation value to a material class and substitution thereof with a modified X-ray attenuation value corresponding to the material class. A material class herein represents a particular material, in particular a biological tissue. Since the aforementioned different materials have different X-ray attenuation characteristics, taking account of the emission spectrum used for recording the at least one projection data set, different local X-ray attenuation values can be assigned to different material classes. For example, a material class can cover a particular value range for the X-ray attenuation. Each local X-ray attenuation value within this value range is assigned to this material class. Accordingly, a specific modified X-ray attenuation value can also be assigned to each material or tissue. The substitution is carried out particularly easily by way of a look-up procedure. For this purpose, modified X-ray attenuation values are stored for each of the material classes, for example, in the form of a table. The X-ray attenuation values stored are selected, for example, so that they enable a reproduction which is particularly realistic and corresponds to an actual X-ray projection. For this purpose, the energy-dependency of the X-ray attenuation of the different materials can be taken into account, as described in detail below. To this end, for a material class, a plurality of modified X-ray attenuation values can be stored for different desired energy values or energy spectra and can be selected depending on the emission spectrum to be simulated. Alternatively, a falsification of the image content is achieved through the selection of the modified X-ray attenuation value.

According to a further embodiment of the invention, the at least one local X-ray attenuation value is assigned to one of the following material classes: bone, soft tissues, contrast medium. Local X-ray attenuation values assigned to these material classes can be distinguished and thus classified particularly easily in the image data set, depending on the recording modality used and the scan parameters used.

According to a further embodiment of the invention, at least one of the modified X-ray attenuation values corresponding to one material class amounts to 0. In other words, the material assigned to the material class is assumed to be a material not interacting with the X-ray radiation. Due to the assignment of this modified X-ray attenuation value, a falsified X-ray projection can advantageously be generated which contains no more information regarding the X-ray attenuation of the material of the associated material class. For example, X-ray projections of this type can be generated which no longer contain bones.

According to a further embodiment of the invention, at least one of the modified X-ray attenuation values corresponding to a material class is selected depending on a pre-determinable virtual X-ray quantum energy distribution. A pre-determinable virtual X-ray quantum energy distribution is to be understood as an X-ray radiation spectrum or an emission spectrum of a virtual X-ray radiation source. This X-ray quantum energy distribution can be pre-determined in the sense that, as described in greater detail below, it can be selected, specified or determined by a computer system of an X-ray imaging device according to at least one embodiment the invention, or input by a user. This X-ray quantum energy distribution is virtual because no projection data set is generated therewith by scanning, rather the modified projection data set is calculated. In other words, through the exchange of the at least one local X-ray attenuation value by way of the modified X-ray attenuation value, the acquisition of a projection data set for the pre-definable virtual X-ray quantum energy distribution is simulated. The pre-determinable virtual X-ray quantum energy distribution consequently corresponds to the X-ray quantum energy distribution actually desired by the user for the recording of the X-ray projection.

In some example embodiments of the present invention, this deviates from the emission spectrum used for the recording of the at least one projection data set. This aspect advantageously takes account of the energy-dependency of the X-ray attenuation of different materials so that, by taking account of the X-ray quantum energy distribution coming into use in a real projection recording, particularly realistic, virtual X-ray projections can be generated.

According to one embodiment, the pre-determinable virtual X-ray quantum energy distribution is given by just one energy value. In the event that all the local X-ray attenuation values are replaced by modified X-ray attenuation values corresponding to this distribution, the virtual X-ray projection generated relates to a monochromatic image. In particular, the pre-determinable virtual X-ray quantum energy can be understood as the mean energy of an emission spectrum of a virtual X-ray radiation source with which an X-ray image corresponding to the virtual X-ray projection would have been generated.

According to another embodiment, the pre-determinable virtual X-ray quantum energy distribution is given by a narrow energy band, for example, an energy band of 5 keV, 10 keV, 15 keV or the like and the virtual X-ray projection corresponds, in the case of the substitution of the local X-ray attenuation values, to a polychromatic image. Alternatively, the X-ray quantum energy distribution relates to an arbitrary, purely notional distribution if special image effects deviating from reality are desired. For this purpose, also, correspondingly modified X-ray attenuation values are stored in the form of a table.

According to a further embodiment, the pre-determinable virtual X-ray quantum energy distribution differs from the emission spectrum which is used for the recording of the at least one projection data set. In particular, in this case, the pre-determinable virtual X-ray quantum energy distribution has no overlap with the emission spectrum. In the context of the simple realization of an embodiment of the invention described above, by way of a look-up procedure, for each material class a plurality of modified X-ray attenuation values corresponding to different pre-determinable, virtual X-ray quantum energy distributions can be stored.

According to another embodiment of the present invention, the modification of the image data set comprises a determination of the material composition in at least one part of the body region of the patient to be imaged. For this purpose, a per se known material or base material analysis is carried out as described in detail, inter alia, in the publication by J. F. Williamson et al., "On two-parameter models of photon cross sections: application to dual-energy CT imaging", Med. Phys. 33 (2006), 4115-4129, the entire contents of which are hereby incorporated herein by reference. The disclosures made there are expressly included in the present disclosure.

This embodiment of the invention enables, firstly, a precise consideration of the materials when generating the modified image data set in at least the part of the body region to be imaged for which the material composition is determined. Secondly, this procedure is suitable to a particular degree for modification of image data sets which do not permit assignment of local X-ray attenuation values to pre-determined material classes, for example, on the basis of the emission spectrum used for the recording of the at least one projection data set or included image artifacts.

According to a further embodiment of the invention, the determination of the material composition takes place on the basis of two projection data sets recorded via the X-ray imaging device, each according to a previously stipulated X-ray quantum energy distribution, wherein the previously stipulated X-ray quantum energy distributions differ from one another. The X-ray quantum energy distributions used for recording the projection data sets are arbitrary and, in particular, are pre-determined or firmly set in advance by way of the X-ray imaging device used and its one or more acceleration voltages or other system parameters.

According to one example, they deviate from the X-ray quantum energy distribution desired by or familiar to the user for the X-ray projection. The material analysis proceeds from the consideration that a local X-ray attenuation value measured by way of an X-ray imaging device with an X-ray quantum energy distribution specified in advance according to a particular emission spectrum can be described as a linear combination of X-ray attenuation values of so-called base materials. Measured X-ray attenuation values result from the at least two projection data sets at different X-ray quantum energy distributions.

The material analysis can be carried out in the image space or the projection space, wherein for the first case separate image data sets must be generated from the projection data sets by way of known reconstruction steps. The material or base material can be any substance or any desired tissue, particularly water, contrast medium such as iodine, soft tissue, bone or the like. The X-ray attenuation of a base material as a function of the energy of the X-ray radiation and thus for every arbitrary previously specified X-ray quantum energy distribution is fundamentally known or can be determined through prior measurements on phantoms and stored in the form of tables for calling up in the context of the material analysis. The result of the material analysis is a spatial density distribution of the at least two materials in the patient, from which for each volume element in the body region of the patient to be imaged, the base material proportions or the base material combination can be determined. In this way, an embodiment of the present invention makes use of the advantages of multispectral computed tomography for generating a realistic X-ray projection.

According to a further embodiment of the invention, the at least one modified X-ray attenuation value is determined depending on a pre-determinable virtual X-ray quantum energy distribution and the material composition determined. On the basis of the known, energy-dependent X-ray attenuation of the at least two materials, by way of addition of the X-ray attenuation values of the two materials weighted according to the material proportions to a pre-determinable, virtual X-ray quantum energy distribution, a modified X-ray attenuation value can be calculated which describes an effective X-ray attenuation that would have resulted from a real X-ray projection with said pre-determinable virtual X-ray quantum energy distribution and subsequent image reconstruction for the volume element under observation.

According to one embodiment, in order to determine the modified X-ray attenuation value, an energy-dependent weighting can also take place during the addition of the X-ray attenuation proportions of the pre-determinable virtual X-ray quantum energy distribution. According to one embodiment, the modified X-ray attenuation value results from a plurality of individual X-ray attenuation values at discrete X-ray quantum energy values within the pre-determinable virtual X-ray quantum energy distribution. In this way, in order to generate a particularly realistic-seeming virtual X-ray projection, the X-ray quantum energy distribution which would have been used for generating the real X-ray projection is taken into account and which typically deviates from the emission spectra in computed tomography.

According to a further embodiment of the invention, at least two local X-ray attenuation values are each replaced with a modified X-ray attenuation value which is selected depending on a pre-determinable virtual X-ray quantum energy distribution, wherein the at least two pre-determinable virtual X-ray quantum energy distributions differ from one another. In other words, according to this embodiment, the X-ray attenuation of a volume element can be modified in relation to a first pre-determinable virtual X-ray quantum energy distribution and another volume element in relation to at least one second pre-determinable virtual X-ray quantum energy distribution. In other words, the modification of the image data set takes place voxel-wise with modified X-ray attenuation values in relation to different pre-determinable virtual X-ray quantum energy distributions. This procedure is particularly advantageous in order to take account of a specific radiation characteristic of a virtual X-ray radiation source to be modeled, or to achieve a disassociation effect in particular regions of the virtual X-ray projection (e.g. artificial suppression or emphasis of bones, contrast medium or soft tissues, inversion of the signal attenuation, so that light regions appear dark and dark regions appear light, etc.).

According to a further embodiment of the invention, the virtual projection geometry assumes parallel virtual X-ray beams or conical virtual X-ray beams. The virtual beams each extend from a notional beam focus of an X-ray radiation source to a detector element of the virtual X-ray radiation detector. The virtual beam or projection geometry corresponds to a purely notional or a real focus position of the virtual X-ray radiation. The assumption of parallel, virtual X-ray beams makes subsequent calculation steps for re-sorting the scan data to the parallel beam geometry ("rebinning") superfluous and prevents image errors caused thereby. The further processing of the projection data sets proves to be particularly simple in the parallel beam geometry.

Alternatively, conical virtual X-ray beams or fan-shaped virtual X-ray beams can be assumed. Parallel beams prove to be particularly useful under the assumption of a virtual X-ray radiation detector with a flat detection surface, as do conical beams in the case of a virtual X-ray radiation detector with a curved detection surface and fan-shaped beams in the case of a linear detector.

According to a further embodiment of the present invention, the forward projection comprises creating line integrals $L_{i,j}$ over the X-ray attenuation values of the modified image data set along a plurality of virtual X-ray beams through the body region of the patient to be imaged via raytracing methods or Fourier methods. Raytracing is herein based on the sampling and weighted summation of the voxels of the voxel space of the CT image data generated by way of weighted, filtered back-projection or any other reconstruction method on the path of an X-ray quantum starting from the virtual X-ray focus to the virtual detector element. The Fourier method is based on the evaluation of the line integrals in the frequency space making use of the Fourier slice theorem.

According to a further embodiment of the invention, the forward projection is carried out taking account of one or more parameters which describe or model the whole physical scan process or the virtual scan process to be emulated. These parameters are, for example, the focus size, focus profile, shaping filter, detector pixel size, scattering processes, etc.

According to a further embodiment, the intensity values are calculated according to the rule $$I_{i,j}=I_{0;i,j}*\exp(-L_{i,j})*\cos(\beta_{i,j})$$

where the indices i,j refer to row and column of a detector element (i,j) of the virtual X-ray radiation detector, $\beta_{i,j}$ is an angle between the observed virtual X-ray beam to the detector element (i,j) and the surface normals n of the virtual X-ray radiation detector and $I_{0;i,j}$ is an X-ray radiation intensity incident upon the detector element (i,j) without X-ray attenuation caused by the patient. The X-ray radiation intensity incident upon the detector element (i,j) without X-ray attenuation $I_{0;i,j}$ caused by the patient is typically not constant across the detector elements due to a variable distance of the beam focus from the detector elements, a possibly anisotropic emission of the virtual X-ray radiation source and/or a possibly used shaping filter. This rule is particularly well suited to the modeling of virtual X-ray radiation detectors with a flat detection surface.

According to a further embodiment of the invention, on calculation of the intensity values, cross-talk behavior of the virtual X-ray radiation detector and/or radiation scattering effects are taken into account. Radiation scattering effects are to be understood as all primary and secondary scattering effects of X-ray quanta outside and inside the patient which impair the image quality with regard to imaging accuracy. Cross-talk behavior of a detector is understood, in general, to be the signal behavior outside the ideally linear response range or lies therein that adjacent detector elements can influence one another in their signal transmission chain. Generally known origins of the cross-talk are the passing across of a light quantum generated in a detector, in the case of scintillation detectors, to another adjacent detector element, as well as electronic interference influences. For this reason, when the line integrals are calculated, an additional convolution step can be provided, on the basis of which the aforementioned effects can be simulated. By taking account of, or simulating, even this type of imaging error as part of the method according to an embodiment of the invention, a particularly realistic image impression of the virtual X-ray projection can be achieved, as would also arise in the actual acquisition of an X-ray projection.

According to a further embodiment of the invention, the transformation of the intensity values into scan values takes account of a signal characteristic line of the virtual X-ray radiation detector. This is configured linear for an ideal virtual X-ray radiation detector and defines the relationship between the intensity of the X-ray radiation incident per detector element and the electrical signal output for this detector element. For a particularly realistic image impression corresponding, for example, to an X-ray film, the signal characteristic line can also deviate from the linear form. In one example, the transformation simulates the blackening of an X-ray film.

According to another embodiment of the present invention, the reconstruction of the image data set takes place with a spatial resolution in the range of 0.1 mm to 0.5 mm. The reconstruction always takes place with a high resolution, since this delimits the beam and detector geometries that come into question. The maximum spatial resolution of the image data set is essentially determined by the size of the detector elements for recording the at least one projection data set. The flat detectors predominantly used nowadays in interventional imaging herein represent the lower limit of the resolution range.

According to another embodiment of the present invention, the scan values assigned to an image matrix are represented as gray values. A suitable gray value range can be selected before the imaging. The selection of a suitable gray value range corresponds to a windowing according to the body region to be imaged and/or the type of investigation. The windowing defines which portion of the Hounsfield scale is assigned to the gray values from black to white in the X-ray projection according to the measured density values, in order thereby to optimize the image contrast of the tissue or materials to be imaged and diagnosed. Thus, for example, a lung window has a width of +/−800 about the center value of −600, a soft tissue window has a width of +/−180 about a center of 60 and a CT angiogram window has a width of +/−450 about a center of 100. Other gray scale windows adapted to the individual case are also possible. Alternatively, a representation of the calculated scan values can also take place in the image matrix in falsified colors. The selection of a suitable gray value window or colors can be carried out automatically by a corresponding unit of the computer system of an X-ray imaging device described in greater detail below, or by a user.

At least one embodiment of the invention also relates to a computer program with program code for carrying out all the method steps in accordance with the method according to at least one embodiment of the invention when the program is run in a computer. As a result, the method can be carried out reproducibly and in a less error-prone way on different computers.

At least one embodiment of the invention relates also to a machine-readable data carrier on which the computer program described above is stored.

At least one embodiment of the invention also relates to an X-ray imaging device for generating a virtual X-ray projection of at least one body region of a patient to be imaged, wherein the X-ray imaging device comprises an X-ray module comprising at least one X-ray radiation source for generating and emitting X-ray radiation in each case with a pre-determined X-ray quantum energy distribution, a detector module comprising at least one X-ray radiation detector for detecting X-ray radiation emitted by the X-ray radiation module and a computer system which, during operation, carries out the method steps as per the method according to at least one embodiment of the invention. The X-ray imaging device is an X-ray device which is configured to record a plurality of X-ray projections from different projection angles, for example, a computed tomography device with a ring-shaped rotating frame or a C-arm X-ray device. The recordings can be generated during a, particularly continuous, rotation movement of a recording unit comprising the X-ray module and a detector module cooperating with the X-ray radiation source. An X-ray radiation source can be, in particular, an X-ray tube with a rotating anode. An X-ray radiation detector for a computed tomography device is, for example, a linear detector with a plurality of rows. An X-ray radiation detector for a C-arm X-ray device is, for example, a flat detector. The X-ray detector can be configured so as to be both energy-resolving and counting.

At least one embodiment of the invention also relates to an X-ray imaging device for generating a virtual X-ray projection of at least a body region of a patient to be imaged, wherein the X-ray imaging device comprises the following units: an X-ray module comprising at least one X-ray radiation source for generating and emitting X-ray radiation, in each case, having a pre-determinable X-ray quantum energy distribution, a detector module comprising at least one X-ray radiation detector for detecting X-ray radiation emitted by the X-ray radiation module, and a computer system comprising an interface unit which is configured to acquire at least one projection data set representing the at least one body region of the patient to be imaged, a reconstruction unit which is configured to reconstruct an image data set from the at least one projection data set, wherein the image data set represents local X-ray attenuation values in the at least one body region of the patient to be imaged, a modification unit which is configured to modify the image data set such that at least one local X-ray attenuation value is replaced by a modified X-ray attenuation value, a projection unit which is configured to generate a modified projection data set by forward projection of the modified image data set to a virtual X-ray radiation detector, taking account of a virtual projection geometry, a calculation unit which is configured to calculate intensity values for a plurality of detector elements of the virtual X-ray radiation detector from the modified projection data set, taking account of the virtual projection geometry, a transformation unit which transforms the calculated intensity values into scan values output by the virtual X-ray radiation detector and an assigning unit which assigns the scan values to an image matrix.

According to a further embodiment of the invention, the X-ray module of the X-ray imaging device comprises at least two X-ray radiation sources for generating and emitting X-ray radiation, each with a pre-determined X-ray quantum energy distribution and a detector module comprising at least two X-ray radiation detectors, respectively for detecting X-ray radiation emitted by one of the X-ray radiation sources. In this context, reference is also made to a dual-source or a multi-source X-ray imaging device. The at least two X-ray radiation sources and corresponding X-ray radiation detectors serve for simultaneous and thus particularly rapid recording of at least two projection data sets.

According to a further embodiment of the invention, the detector module comprises an X-ray radiation detector that is selective for the incident X-ray quanta. Energy-selective should be understood as meaning spectrally resolving or spectrally separating. Energy-selective detectors are configured to classify incident X-ray quanta according to their quantum energy. These detectors have the advantage that they are suitable for simultaneous generation of at least two projection data sets which differ in their X-ray quantum energy distribution, so that only one X-ray radiation source is necessary. According to this embodiment of the invention, the recording of the projection data sets takes place particularly rapidly and without additional dosage exposure for the patient.

Energy-selective detectors are, for example, quantum-counting detectors or two-layer detectors. A quantum-counting detector is typically a directly-converting detector which converts an incident X-ray quantum directly into an electrical signal by way of a suitable detector material. Quantum-counting detectors can be operated in an energy-resolving manner, wherein the energy resolution can be set by way of "binning". In other words, arbitrary energy ranges can be set in relation to which, incident X-ray quanta can be classified. The at least two projection data sets are each formed by way of signals within one or more energy ranges. The semiconductors cadmium telluride, cadmium zinc telluride or gallium arsenide or, in the case of a flat detector, amorphous selenium or the like in particular are suitable as detector materials for quantum-counting detectors. A two-layer detector or a dual or double-layer detector is equipped to break down the incident X-ray tube spectrum into a low-energy portion and a high-energy portion. For this purpose, the two-layer detector is constructed from two layers. A detector layer facing toward the X-ray radiation source measures photons of the incident X-ray radiation with lower energy and assigns the measured signals to the first projection data set. It is passed through by high-energy X-ray radiation. Photons with a higher quantum energy are measured in the detector layer arranged thereunder or therebehind, that is, facing away from the X-ray radiation source and assigned to the second projection data set. Typically, both detector layers comprise a scintillator, as a consequence of which, the two-layer detector is an indirectly-converting detector. Crystals such as caesium iodide, cadmium tungstate or ceramic substances, for example, gadolinium oxy-sulfide or the like are used as the scintillator material.

According to another embodiment of the invention, the at least one X-ray radiation detector is configured as a planar detector. In other words, the X-ray radiation detector is a flat detector, as are used, in particular, in C-arm X-ray devices for interventional imaging.

FIG. 1 shows an X-ray imaging device using the example of an X-ray computer tomograph. The computer tomograph shown here has a recording unit 17 comprising a radiation source 8 in the form of an X-ray source and a radiation detector 9 in the form of an X-ray detector. The recording unit 17 rotates about a system axis 5 during the recording of X-ray projections and, during the recording, the X-ray radiation source emits rays 2 in the form of X-rays. The X-ray radiation source is an X-ray tube. The X-ray radiation detector is a linear detector with a plurality of rows.

During the recording of projections, a patient 3 lies on a patient support 6. The patient support 6 is connected to a support base 4 such that the support base carries the patient support 6 with the patient 3. The patient support 6 is configured to move the patient 3 along a recording direction through the opening 10 of the recording unit 17. The recording direction is typically given by the system axis 5 about which the recording unit 17 rotates during the recording of X-ray projections. During a spiral scan recording, the patient support 6 is moved continuously through the opening 10 while the recording unit 17 rotates about the patient 3 and records projection data. Thus the X-rays describe a helix on the surface of the patient 3.

The X-ray imaging device further comprises a contrast medium administration unit 19. A contrast medium, for example, in the form of an iodine-containing solution can be administered to the patient 3 via an injection needle 20 during the projection recording. The flow rate of the contrast medium can be controlled by the contrast medium administration unit 19 as a function of time according to a defined injection protocol. The contrast medium administration unit 19 can be configured integrally with the X-ray imaging device or can be arranged stationary or mobile in the examination room.

The X-ray imaging device has a computer system 12 in the form of a computer which is connected to a display unit 11, for example, for graphical display of reconstructed X-ray image recordings, for example, the reconstructed image data set or the virtual X-ray projection or for display of selection menus relating to an assignable virtual X-ray quantum energy distribution and an input unit 7. The display unit 11 can be, for example, an LCD, plasma or OLED screen. It can also be a touch-sensitive screen which is configured as an input unit 7. A touch-sensitive screen of this type can be integrated into the image output device or configured as part of a mobile device. The input unit 7 is, for example, a keyboard, a mouse, a touch screen or a microphone for speech input. The input unit 7 can also be configured to recognize movements of a user and to convert them into corresponding commands. By way of the input unit 7, for example, a pre-determinable virtual X-ray quantum energy distribution can be selected by a user.

The computer system 12 is connected to the rotatable recording unit 17 for data exchange. By way of an interface unit 21 and the connection 14, firstly, control signals for the X-ray recording are transferred from the computer system 12 to the recording unit 17. For this purpose, different scan protocols, each matched to an examination type can be stored in a memory store 24 and selected by the user before the projection data recording. The control of the recording unit 17 takes place according to the selected scan protocol. Secondly, recorded projection data, for example, in the form of the at least one projection data set for further processing are acquired via the interface unit 21 in a computer unit 16 which is described in greater detail below. The connection 14 is realized in the known manner cable-bound or cable-free. The computer system 12 is also connected to the contrast medium administration unit 19 for the exchange of control signals, particularly for synchronizing the contrast medium administration with the X-ray image recording. For this purpose, the similarly known cable-free or cable-bound connection 24 is available.

The computer system 12 comprises a reconstruction unit 23 which is configured to reconstruct an image data set from the at least one projection data set according to known reconstruction methods. A data connection exists between the display unit 11 and the reconstruction unit 23, for example, for the transmission and display of the image data set.

The modification unit 16 of the computer system 12 is configured as an image and/or image data processing unit. It is configured to carry out all the computation steps on the image data set in relation to the method according to an embodiment of the invention. In particular, the modification unit 16 is configured to replace a local X-ray attenuation value in the image data set with a modified X-ray attenuation value. For this purpose, the modification unit 16 can, in particular, carry out a material analysis on the basis of the at least two projection data sets.

The memory store 24 of the computer system 12 is configured to store energy-dependent modified X-ray attenuation values for a plurality of base materials. The storage takes place, for example, in the form of tables, wherein for each base material, X-ray attenuation values are stored for different X-ray quantum energies. X-ray attenuation values for non-included X-ray quantum energies can be obtained, for example, via the modification unit 16 by way of known interpolation methods. The modification unit 16 is configured to determine from the stored energy-dependent X-ray attenuation values of the base materials, modified X-ray attenuation values for the image data set. For one material class, alternatively, one or more modified X-ray attenuation values can be stored, wherein each modified X-ray attenuation value for a material class corresponds to another pre-determinable virtual X-ray quantum energy distribution. The modification unit 16 and the memory store 24 are connected accordingly for data exchange. Alternatively, the computer system 12 is connected to an RIS network (RIS=Radiological Information System) or a PACS network (PACS=Picture Archiving and Communication System) for calling up the modified X-ray attenuation values which in this case are stored in the RIS or PACS network. Alternatively, modified X-ray attenuation values are placed in the memory store 24 for a plurality of material classes, also stored in table form.

The modification unit 16 and the output unit 11 or input unit 7 also have a data connection in order, for example, to show to the user a selection menu relating to the desired base materials for selection and/or to be able to receive user-side input. Furthermore, the modification unit 16 can be connected to the display unit 11 and the input unit 7 in order to be able to receive and evaluate user-side input regarding the pre-determinable virtual X-ray quantum energy distribution or to display possible alternatives to the user for selection. Alternatively or additionally, the user can also make input via this connection relating to a material class which is not to be taken into account in the virtual X-ray projection.

The computer system 12 comprises a projection unit 22 which projects the modified image data set according to a desired virtual projection geometry and thereby generates a modified projection data set. The projection unit 22 can derive the virtual projection geometry, for example, from user-side input. For this purpose, the projection unit 22 is also connected to the display unit 11 and the input unit 7. Alternatively, the projection unit 22 can automatically stipulate the virtual projection geometry or display it to the user via said connection for selection.

The computer system also comprises a calculation unit 21 which is configured to calculate the modified projection data set from the projection unit 22 into a plurality of intensity values for a virtual X-ray radiation detector. Herein, it also takes into account the virtual projection geometry. In a transformation unit 15 and an assigning unit 18, the intensity values are transformed, taking account of imaging properties of the virtual X-ray radiation detector, into scan values notionally output by said detector and these are subsequently assigned to an image matrix.

In the present case, the reconstruction unit 23, the modification unit 16, the projection unit 22, the transformation unit 15 and the assigning unit 18 are configured as separate modules which, where required, are in data-exchanging communication with one another. Alternatively, all the other named units can, for example, also be integrated into the modification unit 16, whether in the form of a physical or a functional integrity.

The computer system 12 can cooperate with a computer-readable data carrier 13, in particular, in order to carry out a method according to an embodiment of the invention by way of a computer program with program code. Furthermore, the computer program can be stored on the machine-readable carrier, so as to be callable. In particular, the machine-readable carrier can be a CD, DVD, Blu-Ray disc, memory stick or a hard disc drive. The reconstruction unit 23, modification unit 16, projection unit 22, calculation unit 21, transformation unit 15 and the assigning unit 18 can be configured in the form of hardware or software. For example, the modification unit 16 is configured as an FPGA (Field Programmable Gate Array) or comprises an arithmetic logic unit.

In the example shown here, at least one computer program is stored in the memory store 24 of the computer system 12 which carries out all the method steps of the method according to an embodiment of the invention when the program is carried out on the computer. The computer program for carrying out the method steps of the method according to an embodiment of the invention comprises program code. Furthermore, the computer program can be configured as an executable file and/or can be stored on a computer system other than the computer system 12. For example, the X-ray imaging device can be configured such that the computer system 12 loads the computer program into its internal working memory to carry out the method according to an embodiment of the invention via an intranet or via the internet.

Figure 2:
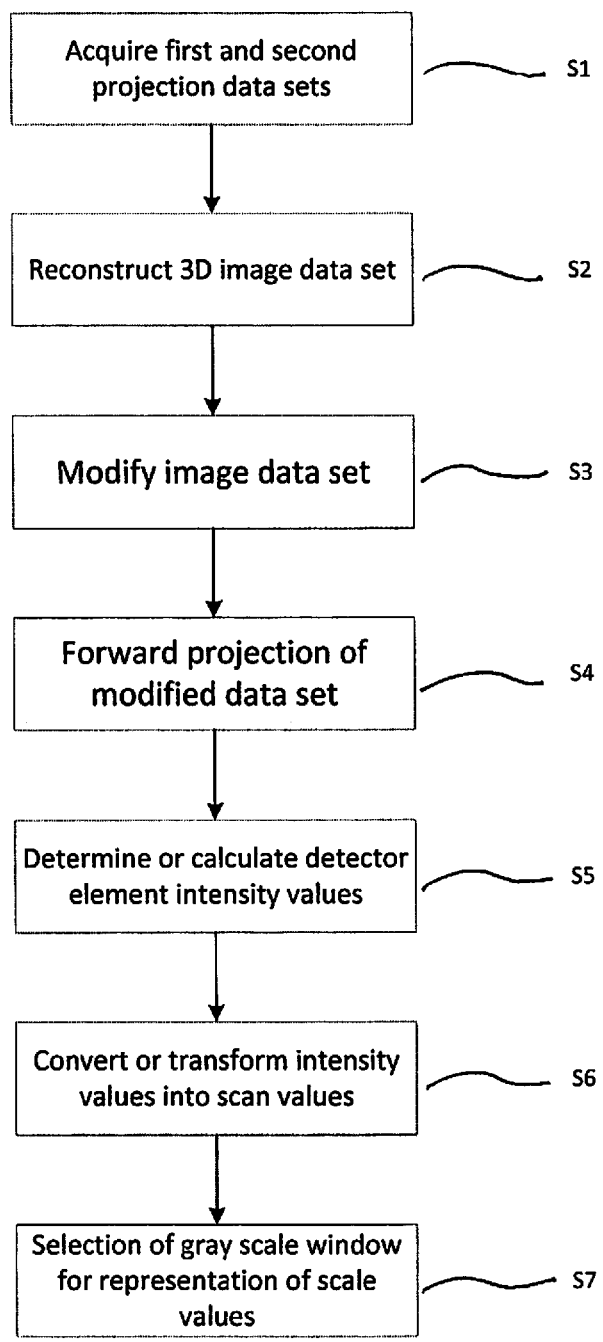
FIG. 2 shows a schematic sequence of the method according to an embodiment of the invention wherein a modification of an image data set takes place.

FIG. 2 shows the method according to an embodiment of the invention in an exemplary embodiment. In a first step S1, a first and second CT projection data set of the patient 3 are acquired by the computer system 12 via the interface unit 21 from the recording unit 17 and transferred to the reconstruction unit 23. The CT projection data sets relate to the thorax of the patient 3. The acquisition of the CT projection data sets can also comprise the recording of the projection data sets with the recording unit 17. The two CT projection data sets were recorded with a dual source computed tomography device with acceleration voltages of 80 kV and 140 kV. Alternatively, the two CT projection data sets can be acquired by way of a quantum counting X-ray radiation detector of another X-ray imaging device. The CT projection data sets therefore differ with regard to the energy spectrum of the X-ray quanta respectively considered.

Figure 3:
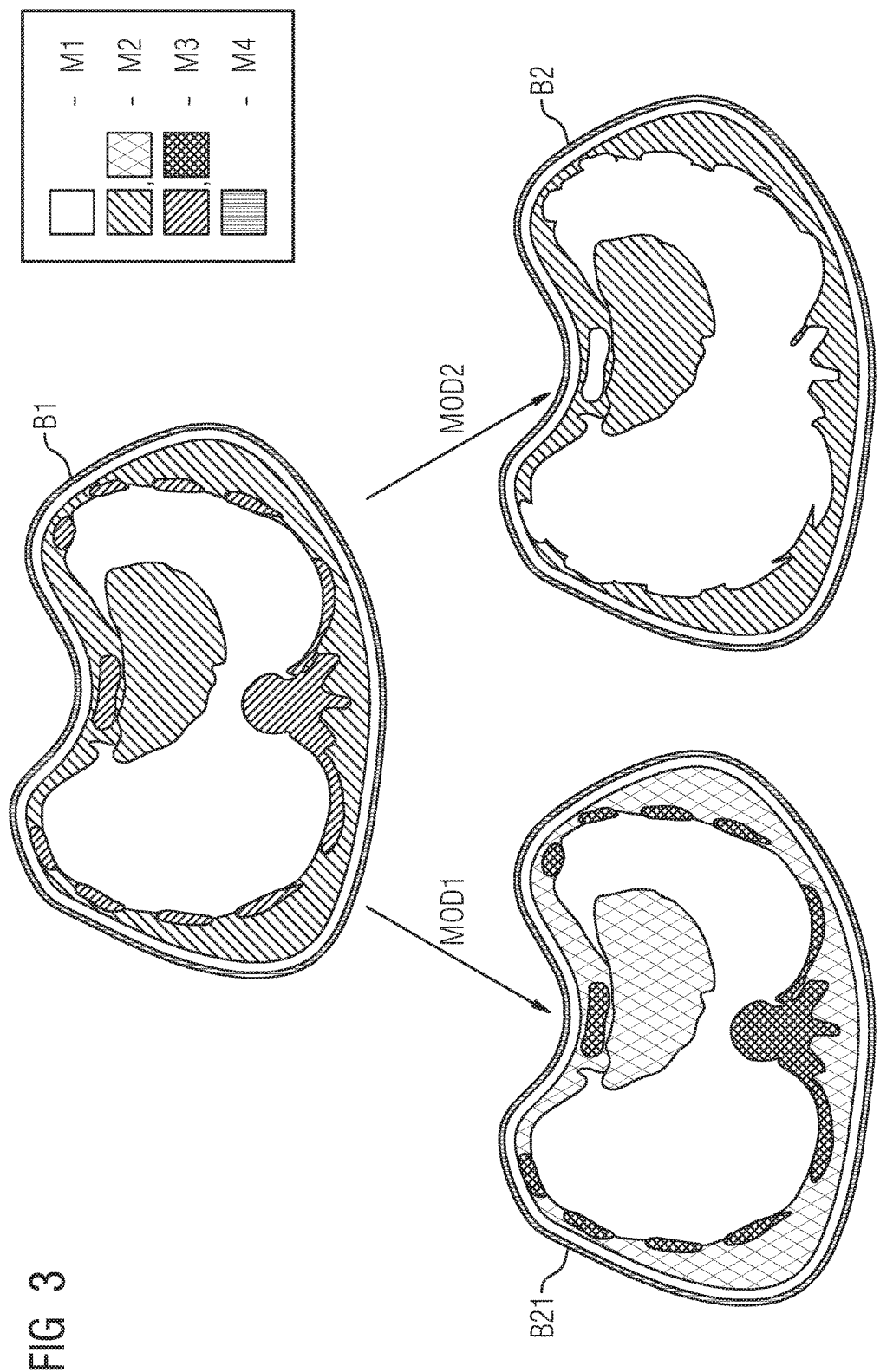
FIG. 3 shows an example sectional representation of the image data set before and after a modification according to the invention, in two embodiments.

The projection unit 23 receives the CT projection data sets and in step S2 reconstructs a three-dimensional image data set B1 from the CT projection data sets, as illustrated by way of example in FIG. 3, based on a transverse sectional image through the thorax of the patient 3. Naturally, the image data set B1 can comprise a plurality of transverse sectional images or can be formed from sectional images lying in other planes. In other words, the reconstruction unit 23 determines a local X-ray attenuation value for each volume element of the patient 3 in the imaged body region. If the local X-ray attenuation values of two adjacent volume elements are, simplistically speaking, identical or nearly identical, both represent the same material but if they differ from one another, they each represent different materials. A material border then extends between the two volume elements.

Represented in the sectional image of the image data set B1, by way of example, are different materials or tissue types M1 to M4, where M1=air (in lung tissue), M2=soft tissue, M3=bone tissue and M4=covering material. The distribution of a material in the image data set B1 is revealed by the local X-ray attenuation values determined. The materials are shown in FIG. 3 for illustration purposes with different coloration or shading which differs from the gray values assigned to a real CT sectional image according to the Hounsfield scale.

The reconstruction takes place in this example by way of an iterative reconstruction algorithm which ensures an advantageous noise reduction in the data of the image data set B1. Any other known reconstruction could come into use in step S2, wherein steps for improving the image contrast or for artifact correction are omitted. The image data set B1 can be calculated from just one of the projection data sets or alternatively, the reconstruction unit 23 takes account of both projection data sets and generates the image data set B1 based on both projection data sets, for example, by creating a (weighted) overlaying of the individual image data sets. Alternatively or additionally, both projection data sets are reconstructed for a subsequent further processing into corresponding image data sets.

In a step S3, a modification of the image data set B1 takes place. According to a first embodiment variant, a modification step MOD 1 for forming a modified image data set B21 is carried out and, according to a second embodiment variant, a modification step MOD 2 for forming a second modified image data set B22 is carried out, as shown in FIG. 3 with exemplary sectional images for the modified image data sets B21, B22.

The modification step MOD 1 comprises an assignment of modified X-ray attenuation values to a plurality of local X-ray attenuation values based on a determination of the material composition and thus enables the generation of a particularly realistic X-ray projection. For this purpose, the modification unit 16 carries out a two-material analysis based on the image data for both projection data sets.

For this purpose, the modification unit 16 can evaluate the scan protocol underlying the projection data set recording and, depending on the investigation type specified therein, can determine two base materials. The modification unit 16 can alternatively analyze the image data with regard to the body region of the patient being imaged and therefrom derive two suitable base materials.

Furthermore, the possibility exists that the modification unit 16 offers the user a selection of possible materials via the display unit 11 and the user specifies the base materials, for example, by mouse click on the display unit 11. In the present case, the materials bone and soft tissues are observed. Now, for each volume element, the base material analysis takes place in an essentially known manner on the basis of the X-ray attenuation distributions of the patient 3 in the image data according to bone and soft tissue in order to determine the density distributions or the proportions of the materials per volume element in the body region being imaged. This can be used in order to determine modified X-ray attenuation values which simulate a realistic X-ray projection recording with X-ray radiation of a defined X-ray quantum energy distribution. The stipulation of the virtual X-ray quantum energy distribution is carried out by the user.

For this purpose, via the display unit 11, a sliding control is displayed to him via the modification unit 16 which control can be displaced by way of the input unit 7 on a bar representing different values for the pre-determinable virtual X-ray quantum energy distribution. By displacing the regulator by way of the input unit 7, for example, by way of an activation of the regulator with a mouse click and displacing the regulator by moving the mouse along the bar, the user can select a virtual X-ray quantum energy distribution which, in his view, is optimal. In this alternative, this represents a discrete X-ray quantum energy value.

In another alternative, the virtual X-ray quantum energy distribution is made up of a plurality of discrete X-ray quantum energy values which lie within an emission spectrum. The emission spectrum corresponds herein to the acceleration voltage which the user would have selected for the actual recording of an X-ray projection.

For this purpose, by way of the modification unit 16 via the display unit 11, a plurality of acceleration voltages are displayed to the user which he can select according to a common procedure via the input unit 7. In this way, the user receives the impression of a normal process sequence. For the selected acceleration voltage, the modification unit 16 determines an emission spectrum and derives the X-ray quantum energy distribution from a plurality of discrete X-ray quantum energy values within the emission spectrum.

For this purpose, emission spectra at different acceleration voltages can be stored in the memory store 24 or in an RIS or PACS network callable by the modification unit 16. The selected X-ray quantum energy distribution is used by the modification unit 16 in order to generate a modified image data set B21 on the basis of the calculated material proportions of the base materials for the pre-determinable virtual X-ray quantum energy distribution.

For this purpose, the modification unit 16 accesses tables for bone and soft tissue placed in the local memory store 24 or in an RIS or PACS network from which it takes or interpolates the respective X-ray attenuation values for the virtual X-ray quantum energy. These are subsequently added, weighted according to the material proportions in each volume element. Replacement of local X-ray attenuation values with the modified X-ray attenuation values in this example does not take place in the volume elements in relation to the materials air and clothing material.

The image data set B21 now has realistic X-ray attenuation values, as would also have been acquired in a real X-ray projection recording. The exemplary method described is transferable without difficulty to a multi-material analysis.

The second modified image data set B22 generated with the alternative modification step MOD2 comprises no further information regarding the bone tissue contained in the image data set B1. For its generation, the modification unit 16 identifies all the volume elements contained in the image data set B1 having a local X-ray attenuation value representing bone tissue and assigns the value 0 to these as the modified X-ray attenuation value.

In the modified image data set B22 generated thus, lung tissue and bone can no longer be distinguished from one another. In addition, other materials can be identified and classified by way of their local X-ray attenuation values and provided with the modified X-ray attenuation values associated with the respective material class. The image data set generated in this way corresponds to a consciously falsified representation of the body region of the patient to be imaged.

In the subsequent step S4, a forward projection of the modified image data set B12, B22 is carried out by the projection unit 22, according to a virtual projection geometry. This can also be input by the user.

In the present case, line integrals are calculated over the X-ray attenuation values of the modified image data set along integral lines according to a parallel beam geometry. On the basis of the acquired, modified X-ray attenuation values, this step emulates the generation of a real projection data set that would have been generated by irradiation with a real X-ray quantum energy distribution corresponding to the pre-determinable virtual X-ray quantum energy distribution. Herein, the rays begin in an X-ray radiation source, pass through the upper body of the patient 3 and each end in a detector element (i,j) of a virtual X-ray detector.

In step S5, intensity values for each detector element (i,j) are determined from the modified projection data set taking account of the selected virtual projection geometry, and are converted into scan values in step S6. Herein, the transformation unit 15 takes account of the specific signal characteristic line of the virtual detector which can also be selected or adapted by the user according to a detector used in reality. In step S7, the user can select a suitable gray scale window in which a representation of the scan values is to take place in an image matrix. Alternatively, the user selects artificial colors.

In the description above, the modification calculation steps are carried out in the image space. This is the preferred procedure in view of the calculation effort needed. However, individual calculation steps can also be executed in the projection space provided the spatial information relating to the local or modified X-ray attenuation values is retained.

Summarizing, the method according to at least one embodiment of the invention offers to the user many usage and modification possibilities so that in many cases, a projection recording that is useful to the user can be generated from an existing image data set.

The aforementioned description is merely illustrative in nature and is in no way intended to limit the disclosure, its application, or uses. The broad teachings of the disclosure can be implemented in a variety of forms. Therefore, while this disclosure includes particular examples, the true scope of the disclosure should not be so limited since other modifications will become apparent upon a study of the drawings, the specification, and the following claims. It should be understood that one or more steps within a method may be executed in different order (or concurrently) without altering the principles of the present disclosure. Further, although each of the embodiments is described above as having certain features, any one or more of those features described with respect to any embodiment of the disclosure can be implemented in and/or combined with features of any of the other embodiments, even if that combination is not explicitly described. In other words, the described embodiments are not mutually exclusive, and permutations of one or more embodiments with one another remain within the scope of this disclosure.

The patent claims filed with the application are formulation proposals without prejudice for obtaining more extensive patent protection. The applicant reserves the right to claim even further combinations of features previously disclosed only in the description and/or drawings.

The example embodiment or each example embodiment should not be understood as a restriction of the invention. Rather, numerous variations and modifications are possible in the context of the present disclosure, in particular those variants and combinations which can be inferred by the person skilled in the art with regard to achieving the object for example by combination or modification of individual features or elements or method steps that are described in connection with the general or specific part of the description and are contained in the claims and/or the drawings, and, by way of combinable features, lead to a new subject matter or to new method steps or sequences of method steps, including insofar as they concern production, testing and operating methods. Further, elements and/or features of different example embodiments may be combined with each other and/or substituted for each other within the scope of this disclosure and appended claims.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

Still further, any one of the above-described and other example features of the present invention may be embodied in the form of an apparatus, method, system, computer program, tangible computer readable medium and tangible computer program product. For example, of the aforementioned methods may be embodied in the form of a system or device, including, but not limited to, any of the structure for performing the methodology illustrated in the drawings.

In this application, including the definitions below, the term 'module' or the term 'controller' may be replaced with the term 'circuit.' The term 'module' may refer to, be part of, or include processor hardware (shared, dedicated, or group) that executes code and memory hardware (shared, dedicated, or group) that stores code executed by the processor hardware.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

Further, at least one embodiment of the invention relates to a non-transitory computer-readable storage medium comprising electronically readable control information stored thereon, configured in such that when the storage medium is used in a controller of a magnetic resonance device, at least one embodiment of the method is carried out.

Even further, any of the aforementioned methods may be embodied in the form of a program. The program may be stored on a non-transitory computer readable medium and is adapted to perform any one of the aforementioned methods when run on a computer device (a device including a processor). Thus, the non-transitory, tangible computer readable medium, is adapted to store information and is adapted to interact with a data processing facility or computer device to execute the program of any of the above mentioned embodiments and/or to perform the method of any of the above mentioned embodiments.

The computer readable medium or storage medium may be a built-in medium installed inside a computer device main body or a removable medium arranged so that it can be separated from the computer device main body. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

The computer programs include processor-executable instructions that are stored on at least one non-transitory computer-readable medium. The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective-C, Haskell, Go, SQL, R, Lisp, Java®, Fortran, Perl, Pascal, Curl, OCaml, Javascript®, HTML5, Ada, ASP (active server pages), PHP, Scala, Eiffel, Smalltalk, Erlang, Ruby, Flash®, Visual Basic®, Lua, and Python®.

None of the elements recited in the claims are intended to be a means-plus-function element within the meaning of 35 U.S.C. § 112(f) unless an element is expressly recited using the phrase "means for" or, in the case of a method claim, using the phrases "operation for" or "step for."

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A method for forming a virtual X-ray projection of at least one body region of a patient to be imaged with an X-ray imaging device, the method comprising:
   acquiring at least one projection data set, representing the at least one body region of the patient to be imaged, with the X-ray imaging device;
   reconstructing an image data set from the at least one projection data set, wherein the image data set represents local X-ray attenuation values in the at least one body region of the patient to be imaged;
   modifying the image data set such that at least one local X-ray attenuation value is replaced by a modified X-ray attenuation value;
   generating a modified projection data set by forward projection of the modified image data set onto a virtual X-ray radiation detector, taking account of a virtual projection geometry;
   calculating intensity values for a plurality of detector elements of the virtual X-ray radiation detector from the modified projection data set, taking account of the virtual projection geometry;
   transforming the calculated intensity values into scan values output by the virtual X-ray radiation detector; and
   forming the virtual X-ray projection by assigning the scan values to an image matrix, wherein the transforming of the calculated intensity values into the scan values takes account of a signal characteristic line of the virtual X-ray radiation detector.

2. The method of claim 1, wherein the modifying of the image data set comprises assigning the at least one local X-ray attenuation value to a material class and substitution thereof with a modified X-ray attenuation value corresponding to the material class.

3. The method of claim 2 wherein, the at least one local X-ray attenuation value is assigned to one of the following material classes: bone, soft tissue, or contrast medium.

4. The method of claim 3, wherein at least one of the modified X-ray attenuation values corresponding to one material class is 0.

5. The method of claim 3, wherein at least one of the modified X-ray attenuation values corresponding to one material class is selected depending on a virtual X-ray quantum energy distribution.

6. The method of claim 2, wherein at least one of the modified X-ray attenuation values corresponding to one material class is 0.

7. The method of claim 2, wherein at least one of the modified X-ray attenuation values corresponding to one material class is selected depending on a virtual X-ray quantum energy distribution.

8. The method of claim 7, wherein at least two local X-ray attenuation values are each replaced with a modified X-ray attenuation value which is selected depending on at least one pre-determinable virtual X-ray quantum energy distribution, and wherein the at least one pre-determinable virtual X-ray quantum energy distribution includes at least two pre-determinable virtual X-ray quantum energy distributions, and wherein the at least two pre-determinable virtual X-ray quantum energy distributions differ from one another.

9. The method of claim 1, wherein the modifying of the image data set comprises determination of a material composition in at least one part of the body region of the patient to be imaged.

10. The method of claim 9, wherein the determination of the material composition takes place based upon at least two projection data sets acquired via the X-ray imaging device, each of the at least two projection data sets being acquired according to a different previously stipulated X-ray quantum energy distribution.

11. The method of claim 10, wherein the modifying of the image data set comprises assigning the at least one local X-ray attenuation value to a material class and substitution thereof with at least one modified X-ray attenuation value corresponding to the material class and wherein the at least one modified X-ray attenuation value is determined depending on a pre-determinable virtual X-ray quantum energy distribution and the determined material composition.

12. The method of claim 9, wherein the modifying of the image data set comprises assigning the at least one local X-ray attenuation value to a material class and substitution thereof with at least one modified X-ray attenuation value corresponding to the material class and wherein the at least one modified X-ray attenuation value is determined depending on a pre-determinable virtual X-ray quantum energy distribution and the determined material composition.

13. The method of claim 12, wherein at least two local X-ray attenuation values are each replaced with a modified X-ray attenuation value which is selected depending on at least one pre-determinable virtual X-ray quantum energy distribution, and wherein the at least one pre-determinable virtual X-ray quantum energy distribution includes at least two pre-determinable virtual X-ray quantum energy distributions, and wherein the at least two pre-determinable virtual X-ray quantum energy distributions differ from one another.

14. The method of claim 1, wherein the virtual projection geometry assumes parallel virtual X-ray beams or conical virtual X-ray beams.

15. The method of claim 14, wherein the forward projection comprises generating line integrals $L_{i,j}$ over the X-ray attenuation values of the modified image data set along a plurality of virtual X-ray beams through the body region of the patient to be imaged by way of raytracing methods or Fourier methods.

16. The method of claim 15, wherein the calculating of the intensity values is carried out according to the rule $$I_{i,j} = I_{0;i,j} * \exp(-L_{i,j}) * \cos(\beta_{i,j})$$

and wherein indices i,j refer to row and column of a detector element [i,j] of the virtual X-ray radiation detector, $\beta_{i,j}$ is an angle between an observed X-ray beam to the detector element [i,j] and the surface normals n of the virtual X-ray radiation detector and $I_{0;i,j}$ is an X-ray radiation intensity incident upon the detector element [i,j] without X-ray attenuation caused by the patient.

17. The method of claim 1, wherein the forward projection is carried out taking account of one or more parameters representing a virtual scan process.

18. The method of claim 17, wherein the calculating of the intensity values is carried out according to the rule $$I_{i,j} = I_{0;i,j} * \exp(-L_{i,j}) * \cos(\beta_{i,j})$$

and wherein indices i,j refer to row and column of a detector element [i,j] of the virtual X-ray radiation detector, $\beta_{i,j}$ is an angle between an observed X-ray beam to the detector element [i,j] and the surface normals n of the virtual X-ray radiation detector and $I_{0;i,j}$ is an X-ray radiation intensity incident upon the detector element [i,j] without X-ray attenuation caused by the patient.

19. The method of claim 1 wherein, on calculating of the intensity values, at least one of cross-talk behavior of the virtual X-ray radiation detector and scattered radiation effects are taken into account.

20. The method of claim 1, wherein the reconstructing of the image data set takes place with a spatial resolution in a range of 0.1 mm to 0.5 mm.

21. The method of claim 1, wherein the scan values are represented in the image matrix as gray values.

22. A non-transitory computer readable medium including computer code which, when executed on a computer, is configured to carry out the method of claim 1.

23. A non-transitory machine-readable data carrier including computer code which, when executed on a computer device, is configured to carry out the method of claim 1.

24. An X-ray imaging device for generating a virtual X-ray projection of at least one body region of a patient to be imaged, the X-ray imaging device comprising:
- an X-ray radiation module including at least one X-ray radiation source to generate and emit X-ray radiation with, for each at least one X-ray radiation source, a determinable X-ray quantum energy distribution;
- a detector module including at least one X-ray radiation detector to detect X-ray radiation emitted by the X-ray radiation module; and
- a computer system configured to, during operation, at least
  - acquire at least one projection data set, representing the at least one body region of the patient to be imaged, with the X-ray imaging device,
  - reconstruct an image data set from the at least one projection data set, wherein the image data set represents local X-ray attenuation values in the at least one body region of the patient to be imaged,
  - modify the image data set such that at least one local X-ray attenuation value is replaced by a modified X-ray attenuation value, generate a modified projection data set by forward projection of the modified image data set onto a virtual X-ray radiation detector, taking account of a virtual projection geometry, calculate intensity values for a plurality of detector elements of the virtual X-ray radiation detector from the modified projection data set, taking account of the virtual projection geometry, transform the calculated intensity values into scan values output by the virtual X-ray radiation detector taking account of a signal characteristic line of the virtual X-ray radiation detector, and form the virtual X-ray projection by assigning the scan values to an image matrix.

25. The X-ray imaging device of claim 24, wherein the X-ray module comprises at least two X-ray radiation sources to generate and emit X-ray radiation, each a determinable X-ray quantum energy distribution, and wherein the detector module comprises at least two X-ray radiation detectors, to respectively detect X-ray radiation emitted by one of the at least two X-ray radiation sources.

26. The X-ray imaging device of claim 24, wherein the at least one X-ray radiation detector is selective for the energy of incident X-ray quanta.

27. The X-ray imaging device of claim 24, wherein the at least one X-ray radiation detector is configured as a planar detector.

28. An X-ray imaging device for generating a virtual X-ray projection of at least one body region of a patient to be imaged, the X-ray imaging device comprising:

an X-ray radiation module comprising at least one X-ray radiation source to generate and emit X-ray radiation with, for each at least one X-ray radiation source, a determinable X-ray quantum energy distribution, and a detector module comprising at least one X-ray radiation detector to detect X-ray radiation emitted by the X-ray radiation module, and a computer system, comprising an interface, configured to acquire at least one projection data set representing at least one body region of a patient to be imaged, at least one processor configured to reconstruct an image data set from the at least one projection data set, wherein the image data set represents local X-ray attenuation values in the at least one body region of the patient to be imaged, modify the image data set such that at least one local X-ray attenuation value is replaced by a modified X-ray attenuation value, generate a modified projection data set by forward projection of the modified image data set onto a virtual X-ray radiation detector, taking account of a virtual projection geometry, calculate intensity values for a plurality of detector elements of the virtual X-ray radiation detector from the modified projection data set taking account of the virtual projection geometry, transform the calculated intensity values into scan values output by the virtual X-ray radiation detector taking account of a signal characteristic line of the virtual X-ray radiation detector, and assign the scan values to an image matrix.

29. The X-ray imaging device of claim 28, wherein the X-ray module comprises at least two X-ray radiation sources to generate and emit X-ray radiation, each a determinable X-ray quantum energy distribution, and wherein the detector module comprises at least two X-ray radiation detectors, to respectively detect X-ray radiation emitted by one of the at least two X-ray radiation sources.

30. The X-ray imaging device of claim 28, wherein the at least one X-ray radiation detector is selective for the energy of incident X-ray quanta.

31. The X-ray imaging device of claim 28, wherein the at least one X-ray radiation detector is configured as a planar detector.

* * * * *